United States Patent [19]

Crawford et al.

[11] 4,419,284
[45] Dec. 6, 1983

[54] PREPARATION OF HALOMETHYL ESTERS (AND RELATED ESTERS) OF PENICILLANIC ACID 1,1-DIOXIDE

[75] Inventors: Thomas C. Crawford, Gales Ferry; Vytautas J. Jasys, New London, both of Conn.

[73] Assignee: Pfizer Inc., New York, N.Y.

[21] Appl. No.: 246,453

[22] Filed: Mar. 23, 1981

[51] Int. Cl.³ ............... C07D 499/00; A61K 31/425
[52] U.S. Cl. ....................... 260/245.2 R; 424/270
[58] Field of Search ............... 260/245.2; 424/270, 424/271

[56] References Cited

U.S. PATENT DOCUMENTS 3,996,235 12/1976 Bentley et al. ............... 260/306.7
4,224,951 1/1981 Bigham ........................ 424/250
4,234,579 11/1980 Barth .......................... 424/246

FOREIGN PATENT DOCUMENTS 882028 9/1980 Belgium .
13617 7/1980 European Pat. Off. .
2044255 10/1980 United Kingdom .

Primary Examiner—Nicholas S. Rizzo
Attorney, Agent, or Firm—Charles J. Knuth; Albert E. Frost; Paul D. Thomas

[57] ABSTRACT

Process for preparation of halomethyl esters (and related esters) of penicillanic acid 1,1-dioxide of the formula

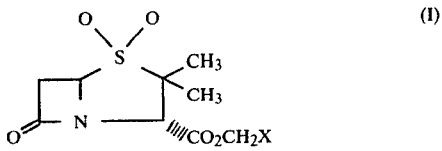

(I)

where X is Cl, Br, I, certain alkylsulfonyloxy or arylsulfonyloxy groups, useful as intermediates in production of antibiotics having beta-lactamase activity, which comprises hydrogenolysis of an ester of the formula

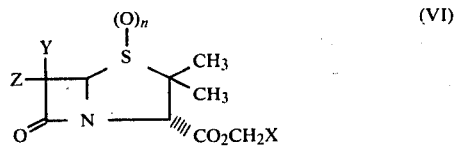

(VI)

where n is zero, 1 or 2; Y and Z are each Cl, Br or I, or Y is H and Z is Cl, Br, I, C≡N— or SCN—, or Y is arylselenyl and Z is Cl or Br; and when n is zero or 1, oxidation of the hydrogenolysis product; a process for preparing compounds of formula (VI, n=2) by oxidation of the corresponding compound (VI) wherein n is zero or 1, and certain novel intermediates useful in the above processes.

8 Claims, No Drawings

PREPARATION OF HALOMETHYL ESTERS (AND RELATED ESTERS) OF PENICILLANIC ACID 1,1-DIOXIDE

BACKGROUND OF THE INVENTION

1. Field of the Invention

The invention relates to processes for preparing halomethyl esters, certain alkylsulfonyloxymethyl esters and arylsulfonyloxymethyl esters of penicillanic acid 1,1-dioxide useful as intermediates in production of antibiotic 6'-acylaminopenicillanoyloxymethyl esters of penicillanic acid 1,1-dioxide; and certain novel 6-substituted and 6,6-disubstituted penicillanate esters and corresponding sulfoxides and sulfones thereof, useful as intermediates in said processes.

2. Description of the Prior Art

U.S. Pat. No. 4,234,579, issued Nov. 18, 1980, discloses penicillanic acid 1,1-dioxide and esters thereof which are readily hydrolyzable in vivo, their use as antibacterial agents and for enhancing the effectiveness of beta-lactam antibiotics against many beta-lactamase producing bacteria. Penicillanic acid, its sulfoxides and certain esters thereof, but not including the halomethyl esters or sulfonyloxymethyl esters, are disclosed as useful intermediates which, upon oxidation, form penicillanic acid 1,1-dioxide.

U.S. Pat. No. 4,244,951, issued Jan. 13, 1981, discloses novel antibacterial agents of formula (X) in which penicillanic acid 1,1-dioxide is linked to known penicillin antibiotics via a methylenedioxo group, i.e.,

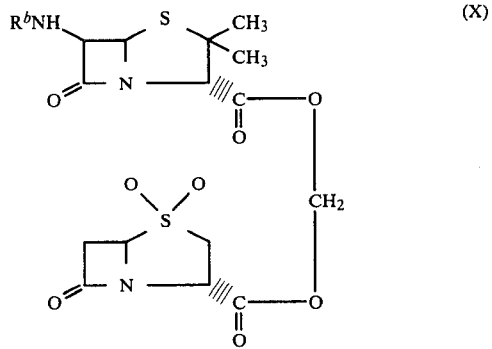

where $R^b$ is the acyl group of a natural or semisynthetic penicillin. The compounds (X) are prepared, for example, by reacting a carboxylate salt of the penicillin such as the sodium, potassium or tertiary amine salt with a halomethyl ester (or related ester) of penicillanic acid 1,1-dioxide. The intermediate halomethyl esters are prepared by esterification of penicillanic acid 1,1-dioxide.

Netherlands patent application No. 8,000,775, published Aug. 15, 1980 and corresponding British patent application No. 2,044,255, also disclose compounds of formula (X) which may be prepared from intermediates of formula (I). The compounds of formula (X) and (I) are prepared in the same manner as disclosed in U.S. Pat. No. 4,244,951. These applications also disclose chloromethyl 6,6-dibromopenicillanic acid, and compounds of the formula

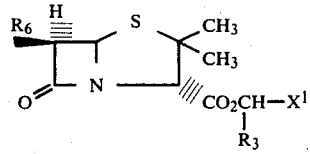

where $R_3$ is H or $CH_3$, $X^1$ is a leaving group such as halogen and $R_6$ is a halogen atom. Halomethyl esters of 6-alpha-chloro- (and 6-alpha-bromo)-penicillanic acid 1,1-dioxide, prepared by esterification of the corresponding 6-alpha-halopenicillanic acid 1,1-dioxides, are also disclosed.

European patent application No. 13,617, published July 23, 1980, discloses a process for preparing beta-lactamase inhibitors of the formula (XII) and a process for their preparation from intermediates (XI)

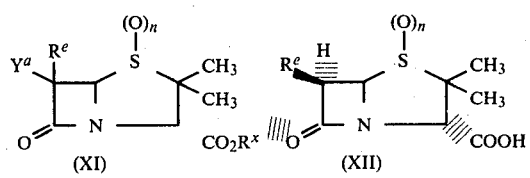

where $R^e$ is (inter alia) H or halogen, n is zero, 1 or 2; $Y^a$ is isocyano when $R^e$ is H, and $Y^a$ is arylselenyl when $R^e$ is chloro; $R^x$ is H or a carboxyl-blocking group, including certain tertiary amine salts and certain compatible ester-forming radicals such as benzyl, certain substituted benzyl, certain tertiary alkyl, 2,2,2-trichloroethyl, trimethylsilyl or trialkyltin esters, by treating the compound (XI) with a triaryltin hydride, dialkyltin hydride or a trialkyltin hydride and thereafter optionally carrying out one or more of the following steps:

(i) converting a sulfide (n=0), sulfoxide (n=1), or sulfone (n=2) to a different such group;

(ii) removing the carboxyl-blocking group if present;

(iii) converting the free acid into a pharmaceutical acceptable salt thereof.

U.S. Pat. No. 3,996,235 discloses 6-isocyano (C≡N—) substituted penicillins, the corresponding sulfoxides, carboxylate salts and esters thereof, as well as methods for their preparation from the corresponding 6-beta-formylaminopenicillanate by reaction with phosgene in the presence of an acid acceptor. The products are isolated as mixtures of 6-alpha-isocyano- and 6-beta-isocyanopenicillianates.

Barton et al., Journal of the Chemical Society (London), Perkin I, 2657 (1980) disclose the use of tri-n-butyltin hydride in hydrogenolysis of isonitriles and isothiocyanates derived from aminoglycosides to provide the corresponding hydrocarbons.

6-Halopenicillanic acids have been disclosed by Cignarella et al., Journal of Organic Chemistry, 27, 2668 (1962) and in U.S. Pat. No. 3,206,469; hydrogenolysis of 6-halopenicillanic acids to penicillanic acid is disclosed in British patent specification No. 1,072,108.

Harrison et al., Journal of the Chemical Society (London), Perkin I, 1772 (1976) disclose: (a) the oxidation of 6,6-dibromopenicillanic acid with m-chloroperbenzoic acid, to give a mixture of the corresponding alpha- and beta-sulfoxides; (b) oxidation of methyl 6,6-dibromopenicillanate with m-chloroperbenzoic acid to give a methyl 6,6-dibromopenicillanate 1,1-dioxide; (c) oxidation of methyl 6-alpha-chloropenicillanate with m-chloroperbenzoic acid, to give a mixture of the corresponding alpha- and beta-sulfoxides; and (d) oxidation of methyl 6-bromopenicillanate with m-chloroperbenzoic acid, to give a mixture of the corresponding alpha- and beta-sulfoxides.

Clayton, Journal of the Chemical Society (London) (C), 2123, (1969), discloses: (a) the preparation of 6,6-dibromo- and 6,6-diiodopenicillanic acid; (b) oxidation of 6,6-dibromopenicillanic acid with sodium periodate, to give a mixture of the corresponding sulfoxides; (c) hydrogenolysis of methyl 6,6-dibromopenicillanate to give methyl 6-alpha-bromopenicillanate; (d) hydrogenolysis of 6,6-dibromopenicillanic acid, and its methyl ester, to give penicillanic acid and its methyl ester, respectively; and (e) hydrogenolysis of a mixture of methyl 6,6-diodopenicillanate and methyl 6-alpha-iodopenicillante to give pure methyl 6-alpha-iodopenicillanate.

Belgian Pat. No. 882,028, granted Sept. 9, 1980, discloses a process for preparing penicillanic acid 1,1-dioxide and its readily hydrolyzable in vivo esters by oxidation of a 6-halopenicillanate or a 6,6-dihalopenicillanate to the corresponding 1,1-dioxide, then dehalogenation to provide the desired penicillanate 1,1-dioxide.

SUMMARY OF THE INVENTION

The present invention relates to a process for preparation of halomethyl esters and sulfonyloxymethyl esters of penicillanic acid 1,1-dioxide of the formula

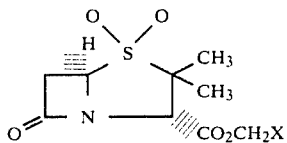

wherein X is Cl, Br, I or $OSO_2R^1$ where $R^1$ is alkyl having from one to six carbon atoms or $C_6H_4R^2$ where $R^2$ is H, Cl, Br, I, $NO_2$ or alkyl or alkoxy having from one to three carbon atoms. The compounds of formula (I) are useful intermediates for production of valuable antibiotics of the formula (X), above. The latter compounds are particularly useful in combatting infections due to beta-lactamase producing bacteria. Particularly valuable compounds (X) are e.g., those wherein $R^b$ is 2-amino-2-phenylacetyl, 2-amino-2-(4-hydroxyphenyl)acetyl, 2-carboxy-2-phenylacetyl, and pharmaceutically acceptable salts thereof.

The invention process, which has significant advantages over the prior art methods for preparing compounds of formula (I), comprises the steps of (1) reacting a compound of the formula

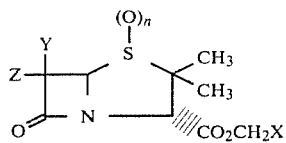

wherein X is as defined above for compound (I), n is zero, 1 or 2; Y and Z are each Cl, Br or I, or Y is H and Z is a member selected from the group consisting of Cl, Br, I, C≡N— (isocyano) and SCN— (isothiocyanato), or Y is $SeC_6H_4R^2$ where $R^2$ is as defined above, and Z is Cl or Br; in the presence of reaction inert solvent with a reducing agent selected from:

(a), a member selected from the group consisting of triaryltin hydrides, dialkyltin dihydrides and trialkyltin hydrides where said aryl is phenyl or phenyl substituted by alkyl or alkoxy having from one to three carbon atoms, hydroxy or nitro, and each of said alkyl groups having from one to six carbon atoms; or (b), hydrogen and a noble metal catalyst; such that when Y and Z are each Cl, Br or I or Y is H and Z is Cl, or I, said reducing agent is (a) or (b), and when Y is H and Z is C≡N— or SCN—, or Y is $SeC_6H_4R^2$ and Z is Cl or Br, said reducing agent is (a), to provide a compound of the formula

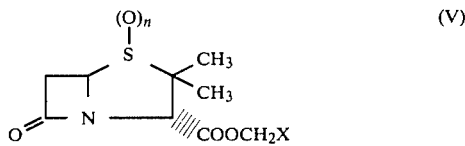

and (2) when n is zero or 1, reacting the compound provided in step (1) with an oxidizing agent selected from sodium permanganate, calcium permanganate, potassium permanganate, hydrogen peroxide in the presence of certain transition metal catalysts, peracetic acid or m-chloroperbenzoic acid; in the presence of reaction inert solvent.

Preferred hydride reducing agents (a) employed in carrying out step (1) with compounds of formula (VI) are triphenyltin hydride and tri-n-butyltin hydride, the latter being especially preferred. Preferably, when the hydride reducing agents are employed, the reduction is carried out in the presence of a radical initiator. Examples of suitable radical initiators are ultraviolet light, di-t-butyl peroxide and azobisisobutyronitrile. A preferred temperature for the reaction with said hydrides is from about 0° C. up to the boiling point of the reaction inert solvent. An especially preferred range of temperature is from about 60° up to the boiling point of the solvent.

When the reducing agent employed in step (1) is (b), hydrogen and a noble metal catalyst, it is preferred to employ noble metal catalysts such as nickel, palladium, platinum and rhodium. An especially preferred noble metal catalyst is palladium. The reaction is preferably carried out in the presence of a reaction inert solvent, at a pressure in the range of from about atmospheric pressure to about 100 kg./cm.² (1400 psi) at a temperature of from about 0° to 60° C.

In step (2) preferred oxidizing agents are potassium permanganate, m-chloroperbenzoic acid and hydrogen peroxide in the presence of certain transition metal catalysts. A preferred temperature for the oxidation step is in the range of from about −30° to 60° C.

Particularly preferred values for n are zero and 2.

The invention also provides a process for preparing 1,1-dioxo intermediates of formula

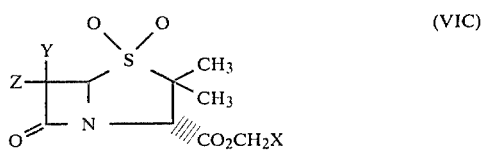

wherein X, Y and Z are as defined above for compound (VI) which comprises reacting a sulfide or sulfoxide of the formula

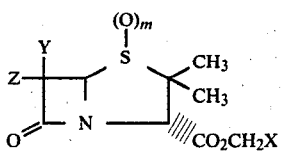 (VID)

wherein m is zero or 1 with an oxidizing agent selected from potassium permanganate, sodium permanaganate, calcium permanganate, hydrogen peroxide in the presence of certain transition metal catalysts, peracetic acid or m-chloroperbenzoic acid in the presence of a reaction inert solvent at a temperature of from −30° to 60° C.

Particularly preferred values for X are Cl, Br, I, methanesulfonyloxy and 4-toluenesulfonyloxy. An especially preferred value for X is Cl.

Particularly preferred values for Y and Z are:
Y and Z are each Cl, Br or I and
Y is H and Z is Cl, Br, I, C≡N— or SCN—.

Especially preferred such values are Y and Z are the same and are each Br and Y is H and Z is Br.

The invention further provides certain novel intermediates of formula (VI) useful in preparation of the above compounds of formula (I) by a process of the invention. Said novel intermediates are defined by the formula

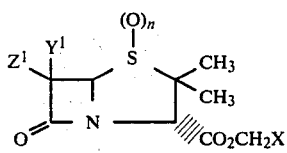 (XIII)

wherein X and n are as defined for compound (VI),
$Y^1$ is H and $Z^1$ is C≡N— or SCN—, or $Y^1$ is $SeC_6H_4R^2$ and $Z^1$ is Cl or Br, $R^2$ is H, Cl, Br, I, $NO_2$ or alkyl or alkoxy having from one to three carbon atoms.

Particularly preferred intermediates (XIII) are those wherein n is zero or 2, $Y^1$ is H and $Z^1$ is C≡N— or SCN—.

More particularly preferred are those compounds (XIII) where n is zero or 2, $Y^1$ is H and $Z^1$ is C≡N— and X is Cl, $CH_3SO_2O$ or $4-CH_3C_6H_4SO_2O$.

Further, the invention provides novel intermediates of the formula

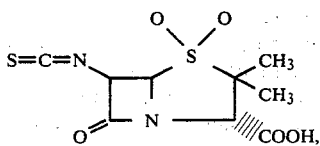 (XIV)

useful in preparation of the corresponding isothiocyanato esters of formula (VI).

Also novel are the intermediate sulfoxides of formula (V, n=1), useful in the preparation of the desired sulfones of formula (I) by oxidation. Especially preferred novel sulfoxide intermediates are:
chloromethyl penicillanic acid 1-oxide,
methylsulfonyloxymethyl penicillanic acid 1-oxide
and p-tolylsulfonyloxymethyl penicillanic acid 1-oxide.

As is known in the art the above sulfoxides exist in both the alpha and beta-configurations and mixtures thereof. Any and all such forms of the above sulfoxides are included herein.

This invention relates to derivatives of penicillanic acid which is represented by the following structural formula:

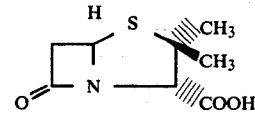

In derivatives of pencillanic acid, broken line attachment (||||||||) of a substituent to the bicyclic nucleus indicates that the substituent is below the plane of the nucleus. Such a substituent is said to be in the alpha-configuration. Conversely, broad line attachment (▬▬) of a substituent to the bicyclic nucleus indicates that the substituent is above the plane of the nucleus. This latter configuration is referred to as the beta-configuration. As used herein a solid line attachment (———) of a substituent to the bicyclic nucleus indicates that the substituent can be in either the alpha-configuration or the beta-configuration.

As used herein a capital letter A, B or C placed after a Roman numeral which designates a particular chemical structure is used to denote values for n of zero, 1 or 2, respectively. Thus, in the above sulfones of formula (VIC), n is 2, the corresponding sulfides wherein n is zero are designated as (IVA) and the corresponding sulfoxides wherein n is 1 are designated (VIB).

DETAILED DESCRIPTION OF THE INVENTION

The invention process for preparing the valuable intermediates of formula (I) is represented by the following reaction sequence

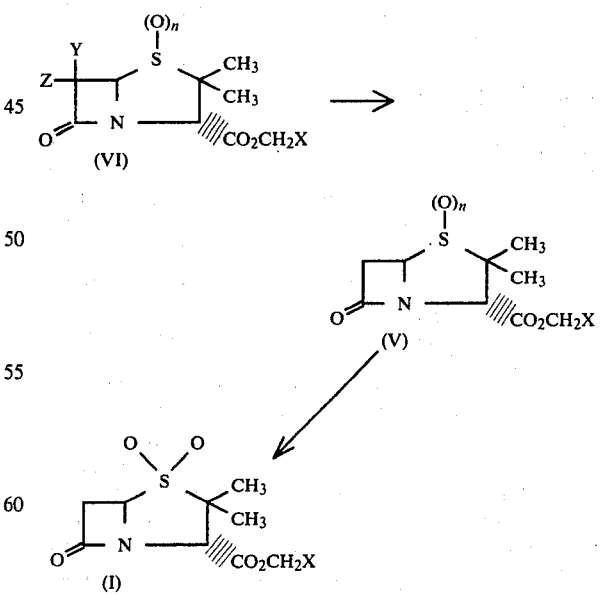

where n, X, Y and Z are as previously defined. When the above process is carried out employing a starting material of formula VIA (n=0) or VIB (n=1) it entails two steps, hydrogenolysis followed by oxidation. However, when a starting material of formula VIC (n=2) is employed only the hydrogenolysis step is employed.

The hydrogenolysis step in each case is carried out employing a reducing agent selected from certain organotin hydrides or hydrogen in the presence of a noble metal catalyst. For those starting compounds of formula (VI) wherein Y is hydrogen or halogen and Z is halogen, either the organotin hydrides or hydrogen and noble metal catalyst may be employed as reducing agent. However, when compounds of formula (VI) are employed wherein Y is hydrogen and Z is isocyano or isothiocyanato, or when Y is $R^2C_6H_4Se$ and Z is Cl or Br, an organotin hydride reducing agent is employed.

Preferred organotin hydride reducing agents are the dialkyltin dihydrides, trialkyltin hydrides, having from one to six carbon atoms in each of said alkyl groups, and the triaryltin hydrides wherein said aryl is phenyl, or phenyl substituted by nitro or alkyl or alkoxy having from one to three carbon atoms. Particularly preferred are triphenyltin hydride and tri-n-butyltin hydride. The latter being especially preferred for reasons of economy and efficiency.

The reaction employing said tin hydrides is ordinarily carried out in the presence of a reaction inert solvent. Suitable solvents for use with the organotin hydride reducing agents are those which substantially dissolve the starting compound of formula (VI) but do not themselves react with the hydride reducing agent. Examples of such solvents include the aromatic hydrocarbons such as benzene, toluene, xylene, chlorobenzene and napthalene; and ethers such as ethyl ether, isopropyl ether, tetrahydrofuran, dioxane and 1,1-dimethoxyethane. Particularly preferred solvents for reasons of economy and efficiency are benzene and toluene.

In carrying out the hydrogenolysis employing organotin hydride reducing agents, when the starting compound of formula (VI) is a 6-substituted compound wherein Y is hydrogen and Z is halogen, C≡N— or SCN— only one mole of a trialkyl- or triaryltin hydride or one-half mole of a dialkyltin dihydride per mole of (VI) is theoretically required. With 6,6-disubstituted compounds of formula (VI) twice the amount of hydride is required by theory. In practice a small excess of hydride, e.g., 5-50% molar excess, is often employed to assure complete reaction.

The hydrogenolysis by organotin hydrides proceeds to substantial completion under the preferred conditions disclosed above without use of a catalyst. However, the reaction is expedited by means of a source of free radicals such as, e.g., ultraviolet light, or a catalytic amount of azobisisobutyronitrile or peroxides such as benzoyl peroxide. A catalytic amount of azobisisobutyronitrile is a preferred source of free radicals for this reaction.

Typically, the compound of formula (VI) is dissolved in reaction inert solvent, the solution is maintained under an inert atmosphere, e.g. a nitrogen or argon atmosphere, and the appropriate amount of organotin hydride and, optionally, the source of free radicals, e.g. azobisisobutyronitrile, added and the resulting mixture stirred at a temperature within the preferred range of from about 0° C. up to the boiling point of the solvent. The reaction is ordinarily complete in from a few minutes to about a few hours, e.g., from 5 minutes at the boiling point of toluene to about 20 hours at 0° C. The product of formula (V) or (I) is then isolated by methods known to those of skill in art. For example, by evaporation of solvent and silica gel chromatography of the residue.

When the hydrogenolysis step is carried out employing hydrogen in the presence of a noble metal catalyst, a convenient method for carrying out this transformation is to stir or shake a solution of a compound of the formula (VI) under an atmosphere of hydrogen, or hydrogen mixed with an inert diluent such as nitrogen or argon, in the presence of a noble metal hydrogenolysis catalyst. Suitable solvents for this hydrogenolysis reaction are those which substantially dissolve the starting compound of the formula (VI) but which do not themselves suffer hydrogenation or hydrogenolysis. Examples of such solvents include ethers such as diethyl ether, tetrahydrofuran, dioxan and 1,2-dimethoxyethan; low molecular weight esters such as ethyl acetate and butyl acetate; tertiary amides such as N,N-dimethylformamide, N,N-dimethylacetamide and N-methylpyrrolidone; water; and mixtures thereof. Additionally, it is often desirable to buffer the reaction mixture so as to operate at a pH in the range from about 4 to 9, and preferably from about 6 to 8. Borate, bicarbonate and phosphate buffers are commonly used. Introduction of the hydrogen gas into the reaction medium is usually accomplished by carrying out the reaction in a sealed vessel, containing the compound of formula (VI), the solvent, the catalyst and the hydrogen. The pressure inside the reaction vessel can vary from about 1 to about 100 kg./cm.$^2$. The preferred pressure range, when the atmosphere inside the reaction vessel is substantially pure hydrogen, is from about 2 to about 5 kg./cm.$^2$. The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 20 hours. The preferred noble metal catalysts used in this hydrogenolysis reaction are the type of agents known in the art for this kind of transformation, for example, nickel, palladium, platinum and rhodium. Palladium is particularly preferred. The catalyst is usually present in an amount from about 0.01 to about 25 weight-percent, and preferably from about 0.1 to about 10 weight-percent, based on the compound of formula (VI). It is often convenient to suspend the catalyst on an inert support; a particularly convenient catalyst is palladium suspended on an inert support such as carbon.

When the hydrogenolysis is substantially complete, the desired product of formula (V) or (I) is then isolated by standard methods, e.g., the catalyst is removed by filtration, the solvent evaporated and the product purified, if desired, by well known methods such as crystallization or by chromatography.

When the product obtained by the above described hydrogenolysis methods is a sulfide or sulfoxide wherein n is zero or 1, respectively, a further oxidation step is required to provide the desired sulfone of formula (I). While a variety of oxidizing agents known in the art to convert sulfides or sulfoxides to sulfones may be employed in this step, preferred oxidants are the alkali metal permanganates, alkaline earth permanganates, hydrogen peroxide in the presence of certain transition metal catalysts and organic peroxycarboxylic acids. Particularly preferred such oxidants are sodium permanganate, potassium permanganate, calcium permanganate, hydrogen peroxide in the presence of certain transition metal catalysts, peracetic acid and m-chloroperbenzoic acid. Especially preferred oxidants are potassium permanganate and m-chloroperbenzoic acid.

When a compound of the formula (V), as defined above wherein n is zero, is oxidized to the corresponding compound of the formula (I), using a metal permanganate, the reaction is usually carried out by treating the compound of the formula (V) with from about 0.5 to about ten molar equivalents, and preferably from about one to about four molar equivalents, of the permanganate in an appropriate, reaction-inert solvent system. When said compound of formula (V) is a sulfoxide wherein m is 1 approximately half the above amount of metal permanganate is ordinarily employed.

An appropriate, reaction-inert solvent system is one that does not adversely interact with either the starting materials or the product, and water is commonly used. If desired, a co-solvent which is miscible with water but will not interact with the permanganate such as e.g., tetrahydrofuran or acetone can be added. The reaction can be carried out at a temperature in the range from about $-30°$ to about $60°$ C., and it is preferably carried out from about $-10°$ to about $10°$ C. At about $0°$ C. the reaction is normally substantially complete within a short period, e.g. within two hours. Although the reaction can be carried out under neutral, basic or acid conditions, it is preferable to operate at a pH in the range from about 4 to about 9. However, it is essential to choose conditions which avoid decomposition of the beta-lactam ring system of the compound of the formulae (V) or (I). Indeed, it is often advantageous to buffer the pH of the reaction medium in the vicinity of neutrality. The product is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula (V) wherein n is zero, is oxidized to the corresponding compound of the formula (I) using a peroxycarboxylic acid, the reaction is usually carried out by treating the compound of the formula (V) with from about 1 to about 6 molar equivalents, and preferably about 2.2 molar equivalents of the oxidant in a reaction-inert organic solvent. As above, only half the amount of peroxycarboxylic acid is required when the corresponding sulfoxides of formula (V) are employed. Preferred such solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about $-30°$ to about $60°$ C., and preferably from about $15°$ to about $30°$ C. At about $25°$ C., reaction times of about 2 to about 16 hours are commonly used. The product is normally isolated by removal of the solvent by evaporation in vacuo. The reaction product can be purified by conventional methods, as described above and in the Examples.

When hydrogen peroxide in the presence of certain transition metal catalysts is employed to oxidize a sulfide or sulfoxide such as the compounds of formula (V) wherein n is 0 or 1 to the corresponding sulfones wherein n is 2, preferred transition metal catalysts are inorganic compounds of tungsten, molybdenum, or zirconium in which the metals are in their highest oxidation state. Examples of such compounds are tungstic acid, sodium tungstate, zirconium tetrachloride and potassium molybdate. The transition metal compounds employed as catalyst are preferably in the form of an aqueous solution or a colloidal suspension. The reaction employing the preferred transition metal catalysts can be carried out over a pH range of about 3 to 9, however a pH of from about 4 to 7 is preferred. When the compound to be oxidized is a sulfide, such as that of formula (V) where n is zero, at least two moles of hydrogen peroxide per mole of said sulfide is required to provide the corresponding sulfone. However, for oxidizing sulfoxides to sulfones or sulfides to sulfoxides, only one mole of hydrogen peroxide is required to afford the desired product. Preferred reaction inert solvents for the oxidation with hydrogen peroxide/transition metal catalyst include the lower alkanols such as methanol, ethanol and isopropanol; ethylene glycol, ethyl acetate, 1,2-dimethoxyethane, water and mixtures thereof. While the oxidation can be carried out over a wide range of temperature, a preferred temperature is in the range from about $20°$ to $60°$ C., at which temperature the oxidation is ordinarily complete in from about two hours to two days, e.g., overnight. The desired product is then isolated and can be purified, if desired, by methods described above and in the Examples.

The present invention also provides a process for preparing 1,1-dioxo intermediates of the formula

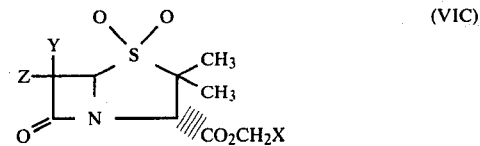

(VIC)

wherein X, Y and Z are as defined above which comprises reacting a sulfide or sulfoxide of the formula

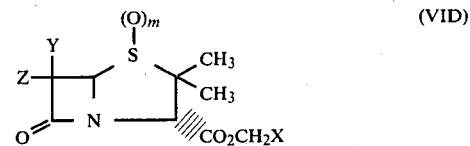

(VID)

wherein m is zero or 1 with an oxidizing agent.

A variety of oxidizing agents known in the art for the conversion of sulfides and sulfoxides to sulfones can be employed in this process. However, preferred oxidants are the same alkali metal permanganates, alkaline earth permanganates, hydrogen peroxide in the presence of certain transition metal catalysts and organic peroxycarboxylic acids, disclosed above for the oxidation of sulfides and sulfoxides of formula (V) to the desired products of formula (I). Furthermore, preferred conditions for use of the preferred oxidants are the same as given above.

The products of formula (VIC) are useful intermediates for preparation of the desired esters of formula (I) by the initial process disclosed above.

The invention further provides certain novel intermediates which are useful in preparation of compounds of formula (I). Said novel intermediates are of the formula

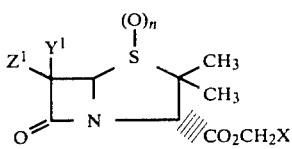

(XIII)

wherein n, X, $Y^1$ and $Z^1$ are as defined above.

The compounds (VI) and (XIII) are obtained, for example, by esterification of the corresponding 3-carboxylate salt of formula (III) with a compound of formula $XCH_2X^2$

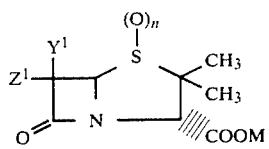

(III)

wherein X and $X^2$ are both leaving groups, X is as previously defined and $X^2$ is X or a better leaving group than X. Preferred values for $X^2$ are I and chlorosulfonyloxy. M is a cation, preferably $Na^+$, $K^+$, $NH_4^+$ or a tetraalkylammonium ion having from one to six carbon atoms in each of said alkyl groups. A preferred tetraalkylammonium ion is tetrabutylammonium. The reaction is carried out in a suitable solvent, e.g., dimethylformamide, ethyl acetate, dichloromethane, acetone or hexamethylphosphoric acid triamide. A preferred temperature for this esterification is from about 0° to 60° C., at which temperature the reaction is substantially completed in from a few hours up to about 24 hours. The desired ester of formula (XIII) is isolated by methods well known in the art. For example, by evaporation of solvent and purification of the crude product, if desired, e.g., by column chromatography.

The compounds of formula (VI) and (XIII) are, alternately, prepared from 6-aminopenicillanate derivatives of the formula

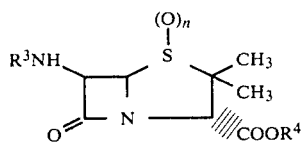

(VII)

wherein n is as defined above, $R^3$ is H, $C_6H_5CH_2CO$ or $C_6H_5OCH_2CO$ and $R^4$ is H or $CH_2X$ where X is as previously defined. For example, for compounds of formula (VI) wherein Y is H, Cl, Br or I and Z is a halogen as defined above or wherein Y is $R^2C_6H_4Se$ and Z is Cl or Br, the carboxylic acid or ester of formula (VII) is converted to an intermediate 6-diazo compound by reaction with nitrous acid (when $R^3$ is H) or dinitrogen tetraoxide (when $R^3$ is $C_6H_5CH_2CO$ or $C_6H_5OCH_2CO$) and the 6-diazo intermediate reacted with a halogen, such as $Cl_2$, $Br_2$, $I_2$, ClBr, ClI or BrI; a hydrogen halide such as HCl, HBr or HI or arylselenylyl chloride or arylselenyl bromide by methods known in the art, see, e.g. Clayton, J. Chem. Soc. (C) 2123 (1969); Sheehan et al., J. Org. Chem., 39, 1444 (1974) and J. Org. Chem. 43, 2203 (1978); European patent Appln. No. 013,617 and U.S. Pat. No. 4,234,579. The 3-carboxylic acids obtained by this method are then esterified as described above for the corresponding salts of formula (III) to provide the desired compound (VI).

Compounds of formula (VI) or (XIII) wherein Y or $Y^1$ is H and Z or $Z^1$ is CN- (isocyano) are prepared e.g., from the corresponding compounds of formula (VII, $R^3$=H) by conversion to the 6-formylamino derivative and its reaction with phosgene in the presence of an acid acceptor, e.g. N-methylmorpholine as disclosed in U.S. Pat. No. 3,996,235. Typically, the reaction is carried out in a reaction inert solvent, e.g. methylene chloride at ambient temperature or lower, preferably at −40° to −50° C. Alternatively, the isonitriles are obtained by reaction of the 6-formylamino compounds with an arylsulfonylhalide, e.g., toluene-p-sulfonyl chloride in the presence of an acid acceptor such as pyridine at a temperature of from about −10° to 50° C., preferably 0° to 30° C. See e.g., Barton et al., J. Chem. Soc. (London) Perkin I, 2657 (1980).

The corresponding isothiocyanato derivatives of formula (VI), (XIII) or (XIV) are prepared from the 6-aminopenicillanates of formula (VII, $R^3$=H), for example by reaction with thiophosgene. The reaction is ordinarily carried out in the presence of a reaction inert solvent at temperatures of from −20° to 50° C. A preferred temperature is from about 0° to 35° C. Preferred reaction inert solvents are the halogenated hydrocarbons, e.g. methylene chloride, chloroform and 1,2-dichloroethane. The desired product is isolated by standard methods, e.g. washing the organic layer with dilute acid and evaporation of solvent.

Another method for preparing the isothiocyanato compounds of formula (VI), (XIII) or (XIV) is that disclosed by Barton et al., loc cit., for conversion of aminoglycosides to isothiocyanates. In this method the amine of formula (VII), $R^3$=H is reacted with equimolar amounts of carbon disulfide and a dehydrating agent, e.g. dicyclohexylcarbodiimide in the presence of reaction inert organic solvent. The reaction is preferably carried out at a temperature of from about −10° to 30° C. Preferred reaction inert solvents include ethyl ether, tetrahydrofuran, benzene, toluene and mixtures thereof. Ethyl ether is an especially preferred solvent.

The 6-isocyanopenicillanic acids, 6-isothiocyanatopenicillanic acids and the corresponding sulfoxides and sulfones, obtained by the above procedures, are converted to esters via their salts of formula (III) as described above, to provide the desired intermediates of formula (VI) and (XIII).

As mentioned above the compounds of formula (I) are useful intermediates for preparation of antibacterial agents of formula (X) disclosed in U.S. Pat. No. 4,244,951 and British patent application No. 2,044,255.

The compounds of formula (X) possess in vivo antibacterial activity in mammals, and this activity can be demonstrated by standard techniques for penicillin compounds. For example, the compound of formula (X) is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula (X). The compounds of formula (X) can be administered by both the oral (p.o.) and subcutaneous (s.c.) route.

The in vivo activity of the antibacterial compounds (X) make them suitable for the control of bacterial infections in mammals, including man, by both the oral and parenteral modes of administration. The compounds are useful in the control of infections caused by susceptible bacteria in human subjects. In general, it is the substituent $R^b$ which determines whether a given bacterium will be susceptible to a given compound of formula (X). A compound of formula (X) breaks down to the corresponding compound of formula (IX) (or salt thereof) and penicillanic acid 1,1-dioxide (VIII) after administration to a mammalian subject by either the oral or parenteral route.

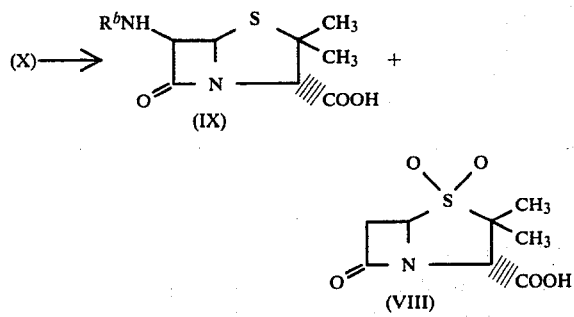

Penicillanic acid 1,1-dioxide then functions as a beta-lactamase inhibitor, and it increases the antibacterial effectiveness of the compound of formula (IX) (or salt thereof). For example, when $R^b$ is 2-phenylacetyl or 2-phenoxyacetyl, the compounds will find use in the control of infections caused by susceptible strains of *Staphylococcus aureus;* when $R^b$ is D-2-amino-2-phenylacetyl, D-2-amino-2-[4-hydroxyphenyl]acetyl, 2-carboxy-2-phenylacetyl, 2-carboxy-2-[2-thienyl]acetyl, 2-carboxy-2-[3-thienyl]acetyl, or 2-[4-ethyl-2,3-dioxopiperazinocarbonylamino]-2-phenylacetyl, the compounds are useful in the control of infections caused by susceptible strains of *Escherichia coli.*

In determining whether a particular strain of *Staphylococcus aureus* or *Escherichia coli* is sensitive to a particular compound of formula (X), the in vivo test described earlier can be used. Alternatively, the minimum inhibitory concentration (MIC) of a 1:1 mixture of the compound of formula (IX) (or its salt) and the compound of formula VIII (or its salt) can be measured. The MIC's can be measured by the procedure recommended by the International Collaborative Study on Antibiotic Sensitivity Testing (Ericcson and Sherris, Acta. Pathologica et Microbiologia Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of formula (X), or a salt thereof, in a mammal, particularly man, the compound can be administered alone, or it can be mixed with other antibiotic substances and/or pharmaceutically-acceptable carries or diluents. Said carrier or diluent is chosen on the basis of the intended mode of administration. For example, when considering the oral mode of administration, the antibacterial compound (X) can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

The antibacterial compounds of formula (X) and pharmaceutically acceptable salts thereof are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds (X) will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Infrared (IR) spectra were measured neat or as potassium bromide discs (KBr discs) and diagnostic absorption bands are reported in wave numbers (cm$^{-1}$). Nuclear magnetic resonance spectra (NMR) were measured at 60 MHz for solutions in deuterated chloroform (CDCl$_3$), D$_2$O or deuterated acetone (CD$_3$COCD$_3$), and peak positions are reported in parts per million downfield from tetramethylsilane. The following abbreviations for peak shapes are used: s, singlet; d, doublet; t, triplet; q, quartet; m, multiplet; dd, double doublet.

EXAMPLE 1

Chloromethyl 6,6-dibromopenicillanate 6,6-Dibromopenicillanic acid (8.0 g., 22 mmole) was stirred with 75 ml. methylene chloride, 35 ml. water was added. To this was added tetrabutylammonium hydroxide to adjust to pH 8. The organic layer was separated, the aqueous phase extracted with 30 ml. methylene chloride. The combined organic layers were evaporated to dryness in vacuo to provide the tetrabutylammonium salt of 6,6-dibromopenicillanic acid, 14.2 g., as a light brown oil. To this was added 40 ml. of chloroiodomethane, and the resulting mixture stirred under nitrogen for three hours at room temperature. The reaction mixture was concentrated in vacuo, the residue stored overnight at room temperature and purified by chromatography on 300 g. silica gel, eluting with 95:5 (by volume) toluene/ethyl acetate. Fractions containing the less polar material were combined and evaporated to afford 5.4 g. (59%) of the desired product, M.P. 105°–106° C. $^1$H-NMR (CDCl$_3$) ppm (delta): 1.6 (s, 3H), 1.75 (s, 3H), 4.62 (s, 1H), 5.8 (dd, 2H), 5.82 (s, 1H).

When the above procedure is repeated, except that the chloroiodomethane used therein is replaced by an equimolar amount of bromoiodomethane, diiodomethane, di(methylsulfonyloxy)methane, di(isobutylsulfonyloxy)methane, di(n-hexylsulfonyloxy)methane, di(benzenesulfonyloxy)methane or a compound of the formula (R$^2$C$_6$H$_4$SO$_2$O)$_2$CH$_2$ where R$^2$ is 4-Cl, 2-Br, 4-I, 3-NO$_2$, 4-CH$_3$, 3-(CH$_3$)$_2$CH, 4-CH$_3$O, 3-C$_2$H$_5$O or 4-n-C$_3$H$_7$O, this affords, respectively:

bromomethyl 6,6-dibromopenicillanate, iodomethyl 6,6-dibromopenicillanate,
methylsulfonyloxymethyl 6,6-dibromopenicillanate,
isobutylsulfonyloxymethyl 6,6-dibromopenicillanate,
n-hexylsulfonyloxymethyl 6,6-dibromopenicillanate,
benzenesulfonyloxymethyl 6,6-dibromopenicillanate,
and R$^2$-C$_6$H$_4$-sulfonyloxymethyl 6,6-dibromopenicillanates where R$^2$ is as defined above for the di(substituted phenylsulfonyloxy)methane reagent.

EXAMPLE 1A

Iodomethyl 6,6-dibromopenicillanate

To 25 ml. of acetone was added 4.15 g. (10.2 mmole) chloromethyl 6,6-dibromopenicillanic acid and 7.5 g. (50 mmole) sodium iodide. The mixture was stirred overnight at room temperature and the acetone was evaporated to afford a dark residue. This was dissolved in 150 ml. ethyl acetate, washed with water (3×25 ml.), saturated brine (25 ml.), dried (MgSO$_4$) and the solvent evaporated in vacuo to yield a residual oil which was purified by chromatography on 100 g. silica gel, eluting with 1:1 (by volume) ethyl acetate/hexane. Thirty milliliter fractions were collected. The product eluted in fractions 4–6, which were combined and evaporated to afford 5.95 g. of colorless oil which crystallized upon standing, M.P. 67°–68° C. $^1$H-NMR (CDCl$_3$) ppm (delta): 1.55 (s, 3H), 1.65 (s, 3H), 4.54 (s, 1H), 5.8 (s, 1H), 5.98 (s, 2H).

EXAMPLE 1B

Employing the appropriate 6-substituted or 6,6-disubstituted penicillanic acid in the procedures of Example 1 and 1A, the following esters are prepared in like manner.

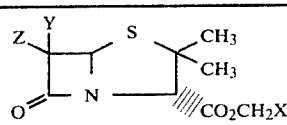

| Y | Z | X |
| --- | --- | --- |
| H | alpha-Br | I |
| H | alpha-Cl | CH$_3$SO$_2$O |
| H | alpha-I | C$_2$H$_5$SO$_2$O |
| H | beta-Cl | (CH$_3$)$_2$CHCH$_2$SO$_2$O |

-continued

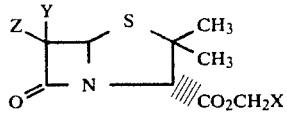

| Y | Z | X |
| --- | --- | --- |
| H | beta-Br | Cl |
| H | beta-I | C$_6$H$_5$SO$_2$O |
| Cl | Cl | 4-CH$_3$C$_6$H$_4$SO$_2$O |
| Cl | Cl | Cl |
| Br | Cl | Cl |
| Cl | I | n-C$_6$H$_{13}$SO$_2$O |
| Cl | I | Cl |
| Br | I | Cl |
| Br | I | CH$_3$SO$_2$O |
| Br | Br | Br |
| I | I | Cl |
| Br | Br | 4-CH$_3$C$_6$H$_4$SO$_2$O |

EXAMPLE 2

Chloromethyl 6,6-dibromopenicillanate 1,1-Dioxide

A solution of 7.1 g. (17.4 mmole) chloromethyl 6,6-dibromopenicillanate in 75 ml. ethyl acetate was cooled to 0° C. and 7.3 g. (36 mmole) of m-chloroperbenzoic acid was added. The mixture was stirred under nitrogen at 0° C. overnight, diluted to 150 ml. with ethyl acetate, and 50 ml. water added at 0° C. Sufficient sodium bisulfite was added to destroy the excess peracid, the mixture adjusted from pH 2 to pH 7.5 with sodium bicarbonate, the organic layer separated and washed with 50 ml. saturated sodium bicarbonate, 50 ml. water and 25 ml. brine. The washed extracts were dried (MgSO$_4$), concentrated to dryness in vacuo and the residue purified by chromatography on 300 g. silica gel, eluting with 9:1 (by volume) toluene/hexane to afford 5.0 g. (65%) of the desired dioxide as a crystalline solid, M.P. 95°–96° C. $^1$H-NMR (CDCl$_3$) ppm (delta): 1.5 (s, 3H), 1.7 (s, 3H), 4.58 (s, 1H), 5.04 (s, 1H), 5.8 (dd, 2H).

Analysis: Calculated for C$_9$H$_{10}$NO$_5$SBr$_2$Cl: C, 24.59; H, 2.29; N, 3.18

Found: C, 24.63; H, 2.49; N, 3.31.

A second, more polar component was isolated from the chromatography column, 0.8 g. This was identified as a 9:1 mixture of the alpha- and betasulfoxides of chloromethyl 6,6-dibromopenicillanate by $^1$H-NMR.

EXAMPLE 2A

Iodomethyl 6,6-dibromopenicillanate 1,1-Dioxide

Method 1 To 40 ml. of acetone was added 0.25 g. (0.5 mmole) iodomethyl 6,6-dibromopenicillanate and the mixture stirred until a solution was obtained, water, 10 ml., was added followed by sufficient concentrated phosphoric acid to adjust the mixture to pH 4.0. Then 158 mg. (1 mmole) powdered potassium permanganate was added and the mixture stirred at room temperature for 1.25 hours. Ethyl acetate, 100 ml. and water, 50 ml., were added. The resulting mixture adjusted to pH 2.0 with 6 N hydrochloric acid and sodium bisulfite added to consume the excess oxidizing agent (pH 2.9). The organic layer was separated, the aqueous phase extracted with 50 ml. ethyl acetate and the combined organic layers were washed with saturated brine (3×25 ml.). After drying over anhydrous sodium sulfate and evaporation of solvent, 0.29 g. of colorless oil was obtained. The oil was purified by chromatography on 25 g. of silica gel eluting with 1:1 ethyl acetate/hexane taking 15 ml. fractions. Fractions 4 and 5 were combined and evaporated in vacuo to yield 0.27 g. (100%) of colorless oil which crystallized upon standing, M.P. 71°–73° C. $^1$H-NMR (CDCl$_3$) ppm (delta): 1.5 (s, 3H), 1.62 (s, 3H), 4.49 (s, 1H), 5.02 (s, 1H), 5.98 (dd, 2H).

Use of an equivalent amount of sodium permanganate or calcium permanganate in place of potassium permanganate in the above procedure afforded the same product in like manner.

Attempts to prepare iodomethyl 6,6-dibromopenicillanate 1,1-dioxide from the chloromethyl ester prepared in Example 2, by treatment with sodium iodide in acetone by the procedure of Example 1A gave iodomethyl 6-alpha-bromopenicillanate 1,1-dioxide. $^1$H-NMR (CDCl$_3$) ppm/delta: 1.55 (s, 3H), 1.70 (s, 3H), 4.43 (s, 1H), 5.2 (d, 1H), 5.75 (d, 1H), 6.0 (dd, 2H).

EXAMPLE 2B

Employing the compounds provided in Example 1B in place of chloromethyl 6,6-dibromopenicillanate in the procedures of Example 2 or 2A provides the corresponding compound of the formula below

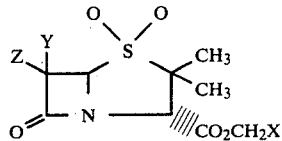

where Y, Z and X are as defined in Example 1B.

EXAMPLE 3

Chloromethyl 6-beta-bromopenicillanate 1,1-Dioxide

To a solution of 3.52 g. (8 mmole) chloromethyl 6,6-dibromopenicillanate 1,1-dioxide in dry benzene (100 ml.), under nitrogen, is added at 0° C., 2.32 g. (8 mmole) tri-n-butyltin hydride. The resulting mixture is stirred overnight at room temperature, the solvent evaporated in vacuo and the residue purified by column chromatography on silica gel to provide the title compound.

Alternately, the same product is obtained by employing chloromethyl 6,6-dibromopenicillanic acid in the above procedure and oxidizing the resulting sulfide, chloromethyl 6-beta-bromopenicillanate, to the sulfone by the procedure of Example 2 or 2A.

EXAMPLE 4

Iodomethyl 6-beta-bromopenicillanate 1,1-Dioxide

A solution of 0.12 g. (0.33 mmole) chloromethyl 6-beta-bromopenicillanate 1,1-dioxide and 0.25 g. (1.66 mmole) sodium iodide in 5 ml. of acetone was stirred 30 hours at room temperature. The resulting pale yellow suspension was evaporated to dryness and the residue taken up in 50 ml. of ethyl acetate, washed successively with 2×10 ml. water, 10 ml. saturated brine and dried over anhydrous sodium sulfate. The resulting solution was evaporated at reduced pressure to obtain the title compound, as a solid, 0.14 g. $^1$H-NMR (CDCl$_3$) ppm (delta): 1.45 (s, 3H), 1.65 (s, 3H), 4.5 (s, 1H), 4.83 (d, 1H), 5.42 (d, 1H), 6.0 (dd, 2H).

EXAMPLE 5

6-alpha-Bromopenicillanic Acid 1,1-Dioxide

To a stirred mixture of 560 ml. of water, 300 ml. of dichloromethane and 56.0 g. of 6-alphabromopenicillanic acid was added 4 N sodium hydroxide solution until a stable pH of 7.2 was achieved. This required 55 ml. of sodium hydroxide. The mixture was stirred at pH 7.2 for 10 minutes and then it was filtered. The layers were separated and the organic phase was discarded. The aqueous phase was then poured rapidly, with stirring, into an oxidizing mixture which had been prepared as follows.

In a 3 liter flask was mixed 63.2 g. of potassium permanganate, 1,000 ml. of water and 48.0 g. of acetic acid. This mixture was stirred for 15 minutes at 20° C. and then it was cooled to 0° C.

After the 6-alpha-bromopenicillanic acid solution had been added to the oxidizing mixture, a cooling bath at −15° C. was maintained around the reaction mixture. The internal temperature rose to 15° C. and then fell to 5° C. over a 20 minute period. At this point, 30.0 g. of sodium metabisulfite was added with stirring over a 10 minute period at about 10° C. After a further 15 minutes, the mixture was filtered, and the pH of the filtrate was lowered to 1.2 by the addition of 170 ml. of 6 N hydrochloric acid. The aqueous phase was extracted with chloroform, and then with ethyl acetate. Both the chloroform extracts and the ethyl acetate extracts were dried using anhydrous magnesium sulfate and then they were evaporated in vacuo. The chloroform solution afforded 10.0 g. (16% yield) of the title compound. The ethyl acetate solution afforded 57 g. of an oil, which was triturated under hexane. A white solid appeared. It was filtered off, giving 41.5 g. (66% yield) of the title compound, M.P. 134° C. (dec.).

Analysis: Calculated for $C_8H_{10}BrNO_5S$: C, 30.78; H, 3.23; Br, 25.60; N, 4.49; S, 10.27%.

Found: C, 31.05; H, 3.24; Br, 25.54; N, 4.66; S, 10.21%.

Oxidation of 6-alpha-chloropenicillanic acid and 6-alpha-iodopenicillanic acid with potassium permanganate, according to the above procedure, affords 6-alpha-chloropenicillanic acid 1,1-dioxide and 6-alpha-iodopenicillanic acid 1,1-dioxide, respectively.

EXAMPLE 6

6-beta-Chloropenicillanic Acid 1,1-Dioxide

An oxidizing solution was prepared from 185 mg. of potassium permanganate, 0.063 ml. of 85% phosphoric acid and 5 ml. of water. This oxidizing solution was added dropwise to a solution of 150 mg. of sodium 6-beta-chloropenicillanic in 5 ml. of water at 0°–5° C., until the purple color of the potassium permanganate persisted. Approximately half of the oxidizing solution was required. At this point, the potassium permanganate color was discharged by the addition of solid sodium bisulfite, and then the reaction mixture was filtered. Ethyl acetate was added to the filtrate and the pH was adjusted to 1.8. The layers were separated and the aqueous layer was further extracted with ethyl acetate. The combined ethyl acetate layers were washed with water, dried and evaporated in vacuo to give 118 mg. of the title compound. The NMR spectrum (in $CD_3COCD_3$) showed absorption at 5.82 (d, 1H), 5.24 (d, 1H), 4.53 (s, 1H), 1.62 (s, 3H) and 1.50 (s, 3H) ppm.

The above product was dissolved in tetrahydrofuran and an equal volume of water was added. The pH was adjusted to 6.8 using dilute sodium hydroxide, the tetrahydrofuran was removed by evaporation in vacuo, and the residual aqueous solution was freeze dried. This afforded the sodium salt of the title compound.

EXAMPLE 7

6-beta-Bromopenicillanic Acid 1,1-Dioxide

To a solution of 255 mg. of sodium 6-beta-bromopenicillanate in 5 ml. of water, at 0° to 5° C., was added a solution prepared from 140 mg. of potassium permanganate, 0.11 ml. of 85% phosphoric acid and 5 ml. of water, at 0° to 5° C. The pH was maintained between 6.0 and 6.4 during the addition. The reaction mixture was stirred at pH 6.3 for 15 minutes, and then the purple solution was covered with ethyl acetate. The pH was adjusted to 1.7 and 330 mg. of sodium bisulfite was added. After 5 minutes, the layers were separated and the aqueous layer was further extracted with ethyl acetate. The combined ethyl acetate solutions were washed with brine, dried ($MgSO_4$) and evaporated in vacuo. This afforded 216 mg. of the title compound as white crystals. The NMR spectrum (in $D_2O$) showed absorptions at 5.78 (d, 1H, J=4 Hz), 5.25 (d, 1H, J=4 Hz), 4.20 (s, 1H), 1.65 (s, 3H) and 1.46 (s, 3H) ppm.

EXAMPLE 8

6-beta-Iodopenicillanic Acid 1,1-Dioxide

Oxidation of 6-beta-iodopenicillanic acid with potassium permanganate, according to the procedure of Example 7, affords 6-beta-iodopenicillanic acid, 1,1-dioxide.

EXAMPLE 9

Chloromethyl 6-alpha-bromopenicillanate 1,1-Dioxide 6-alpha-Bromopenicillanic acid 1,1-dioxide is esterified by the procedure of Example 1 to provide the title compound.

The above procedure is repeated but the chloroiodomethane used therein is replaced by an equimolar amount of bromoiodomethane, diiodomethane, di(methylsulfonyloxy)methane, di(isopropylsulfonyloxy)methane, di(isovalerylsulfonyloxy)methane or a compound of the formula $(R^2C_6H_4SO_2O)_2CH_2$ where $R^2$ is H, 3—Cl, 4—Br, 4—$NO_2$, 4—$CH_3$, 3—n—$C_3H_7$, 4—$CH_3O$, 4—$C_2H_5O$ or 3—$(CH_3)_2CH_2$ to provide, respectively:
bromomethyl 6-alpha-bromopenicillanate 1,1-dioxide,
iodomethyl 6-alpha-bromopenicillanate 1,1-dioxide,
methylsulfonyloxymethyl 6-alpha-bromopenicillanate 1,1-dioxide,
isopropylsulfonyloxymethyl 6-alpha-bromopenicillanate 1,1-dioxide,
isovalerylsulfonyloxymethyl 6-alpha-bromopenicillanate 1,1-dioxide,
and $R^2C_6H_4$-sulfonyloxymethyl 6-alpha-bromopenicillanate 1,1-dioxides where $R^2$ is as defined above.

The corresponding esters of 6-alpha-chloropenicillanic acid 1,1-dioxide; 6-alpha-iodopenicillanic acid 1,1-dioxide; 6-beta-chloropenicillanic acid 1,1-dioxide and 6-beta-iodopenicillanic acid 1,1-dioxide are prepared in like manner.

EXAMPLE 10

Chloromethyl Penicillanate 1,1-Dioxide

A. A mixture of 1.1 g. (2.5 mmole) chloromethyl 6,6-dibromopenicillanate 1,1-dioxide is mixed with 25 ml. each of ethyl acetate and 5% (w/v) sodium bicarbonate and 1.1 g. 10% palladium-on-carbon catalyst is added. The resulting mixture is hydrogenated with agitation at 50 psi (3.5 km/$cm^2$) until the calculated amount of hydrogen is consumed. The catalyst is removed by filtration, the layers separated and the aqueous phase extracted with ethyl acetate. The combined organic layers are dried ($Na_2SO_4$) and evaporated in vacuo to provide 263 mg. (37.5%) of the title compound as a tan solid. $^1$H-NMR ($CDCl_3$) ppm (delta): 1.5 (s, 3H), 1.7 (s, 3H), 3.55 (d, 2H), 4.5 (s, 1H), 4.7 (t, 1H), 5.7 (d, 1H) and 6.0 (d, 2H).

When the palladium catalyst employed above is replaced by a similar amount of nickel, platinum or rhodium catalyst similar results are obtained.

B. Alternatively, the dehalogenation is brought about by contacting the above starting material with a tin hydride as illustrated below:

To a stirred solution of 439 mg. (1 mmole) chloromethyl 6,6-dibromopenicillanate 1,1-dioxide in 50 ml. benzene is added 720 mg. (2.5 mmole) tri-n-butyltin hydride and about 10 mg. azobisisobutyronitrile. The resulting mixture is cooled to 5° C., and irradiated with ultraviolet light while stirring at 0°–10° C. for two hours. The mixture is poured into 100 ml. of cold 5% sodium bicarbonate solution and stirred for thirty minutes. Ethyl acetate is added, the aqueous phase adjusted to pH 7.0, the layers separated and the aqueous phase extracted with fresh ethyl acetate. The combined ethyl acetate solutions are washed with brine, dried ($MgSO_4$) and evaporated in vacuo to afford the title compound. Purification, if necessary, is carried out by silica gel chromatography.

When the tri-n-butyltin hydride used in the above procedure is replaced by an equimolar amount of one of the tin hydrides listed below, comparable results are obtained in like manner.
triphenyltin hydride,
tri-(4-methylphenyl)tin hydride,
tri-(3-methoxyphenyl)tin hydride,
tri-(3-nitrophenyl)tin hydride,
tri-(4-isopropylphenyl)tin hydride,
tri-(2-ethoxyphenyl)tin hydride,
tri-(4-n-propylphenyl)tin hydride,
tri-isobutyltin hydride,
trimethyltin hydride,
triethyltin hydride,
tri-n-amyltin hydride,
tri-n-hexyltin hydride,
tri-(2-methylphenyl)tin hydride,
dimethyltin dihydride,
diisopropyltin dihydride,
di-n-butyltin dihydride,
di-n-hexyltin dihydride.

EXAMPLE 11

Chloromethyl Penicillanate 1,1-Dioxide

A. To a solution of 1.0 g. chloromethyl 6-alpha-bromopenicillanate 1,1-dioxide in 10 ml. methanol is added 3 ml. 1 M sodium bicarbonate and 200 mg. 10% palladium-on-carbon. The reaction mixture is shaken vigorously under a hydrogen atmosphere at 70 psi (5 kg/$cm^2$) until the theoretical amount of hydrogen has been taken up. The mixture is then filtered, the bulk of the solvent removed in vacuo and 20 ml. each of water and ethyl acetate added. The pH of the aqueous phase is adjusted to 8–9, the organic layer is separated, washed with water, dried ($Na_2SO_4$) and evaporated to dryness in vacuo to afford the title compound.

B. To a solution of 360 mg. (1 mmole) chloromethyl 6-alpha-bromopenicillanate 1,1-dioxide in 10 ml. dry toluene is added 5 mg. azobisisobutyronitrile and 305 mg. (1.05 mmole) tri-n-butyltin hydride. The mixture is heated at reflux for 5 minutes, the toluene evaporated in vacuo and the product purified by chromatography on silica gel.

C. Use of an equimolar amount of chloromethyl 6-alpha-chloropenicillanate 1,1-dioxide, chloromethyl 6-alpha-iodopenicillanate, 1,1-dioxide, chloromethyl 6-beta-chloropenicillanate 1,1-dioxide, chloromethyl 6-beta-bromopenicillanate 1,1-dioxide or chloromethyl 6-beta-iodopenicillanate 1,1-dioxide in place of chloromethyl 6-alpha-bromopenicillanate 1,1-dioxide in the above procedures provides the same compound.

EXAMPLE 12

Hydrogenolysis of the appropriate 6,6-dihalopenicillanate 1,1-dioxides provided in Examples 2A and 2B by the procedures of Example 10 or hydrogenolysis of the remaining 6-halopenicillanate 1,1-dioxides provided in Example 9 by the procedures of Examples 10 and 11 provides the following compounds

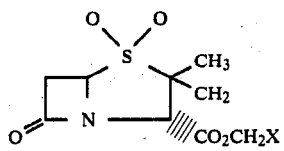

where X is as defined below.

| X | X |
|---|---|
| I | 4-IC$_6$H$_4$SO$_2$O |
| Br | 3-NO$_2$C$_6$H$_4$SO$_2$O |
| CH$_3$SO$_2$O | 3-(CH$_3$)$_2$CHC$_6$H$_4$SO$_2$O |
| C$_2$H$_5$SO$_2$O | 4-CH$_3$OC$_6$H$_4$SO$_2$O |
| (CH$_3$)$_2$CHCH$_2$SO$_2$O | 3-C$_2$H$_5$OC$_6$H$_4$SO$_2$O |
| C$_6$H$_5$SO$_2$O | 4-n-C$_3$H$_7$OC$_6$H$_4$SO$_2$O |
| 4-CH$_3$C$_6$H$_4$SO$_2$O | 3-ClC$_6$H$_4$SO$_2$O |
| n-C$_6$H$_{13}$SO$_2$O | 4-BrC$_6$H$_4$SO$_2$O |
| (CH$_3$)$_2$CHSO$_2$O | 4-NO$_2$C$_6$H$_4$SO$_2$O |
| (CH$_3$)$_2$CH(CH$_2$)$_2$SO$_2$O | 3-n-C$_3$H$_7$C$_6$H$_4$SO$_2$O |
| 4-ClC$_6$H$_4$SO$_2$O | 4-C$_2$H$_5$OC$_6$H$_4$SO$_2$O |
| 2-BrC$_6$H$_4$SO$_2$O | |

EXAMPLE 13

Chloromethyl 6-alpha-Chloropenicillanate

A mixture of 2.35 g. (0.01 mole) 6-alpha-chloropenicillanic acid and 5.0 ml. water is treated with 5.0 ml. 2 N potassium hydroxide. Potassium bicarbonate (6.0 g.), tetrabutylammonium hydrogen sulfate (0.34 g., 0.001 mole), dichloromethane (20 ml.) and chloromethyl chlorosulfate (1.64 g., 0.011 mole) is added and the resulting mixture stirred at 25° to 30° C. for two hours. The reaction mixture is filtered, the layers separated. The organic phase is dried (Na$_2$SO$_4$) and evaporated to dryness to afford the title compound.

The following compounds are made in like manner from the appropriate 6-substituted penicillanic acid:
chloromethyl 6-alpha-bromopenicillanate,
chloromethyl 6-alpha-iodopenicillanate,
chloromethyl 6- beta-chloropenicillanate,
chloromethyl 6-beta-bromopenicillanate,
chloromethyl 6-beta-iodopenicillanate
chloromethyl 6,6-dibromopenicillanate,
chloromethyl 6,6-dichloropenicillanate,
chloromethyl 6,6-diiodopenicillanate,
chloromethyl 6-chloro-6-iodopenicillanate,
chloromethyl 6-bromo-6-iodopenicillanate,
chloromethyl 6-isocyanopenicillanate,
chloromethyl 6-isothiocyanopenicillanate,
chloromethyl 6-chloro-6-phenylselenyl penicillanate.

EXAMPLE 14

Chloromethyl 6-alpha-chloropenicillanate 1-Oxide

To a stirred solution of 8.49 g. (0.03 mole) chloromethyl 6-alpha-chloropenicillanate in 200 ml. chloroform is added at 0° C. a solution of 6.12 g. (0.03 mole) 3-chloroperbenzoic acid in 100 ml. chloroform. Stirring is continued for 1.5 hours at 0°–5° C. The reaction mixture is then filtered, washed with sodium bicarbonate solution, water and dried (Na$_2$SO$_4$). Evaporation of solvent in vacuo affords the crude title compound as a mixture of alpha- and beta-sulfoxides which can be purified, if desired, by chromatography on silica gel.

Alternately, the title compound is prepared by oxidation of 6-alpha-chloropenicillanic acid by oxidation with one equivalent of 3-chloroperbenzoic acid in tetrahydrofuran at 0°–25° C. for about one hour, according to the procedure of Harrison et al., Jour. Chem. Soc. (London), Perkin I, 1772 (1976). The resulting 6-alpha-chloropenicillanic acid 1-oxide is then esterified by the procedure of Example 15 to provide the desired chloromethyl ester.

The remaining 6-substituted penicillanate esters and 6,6-dihalopenicillanate esters provided in Examples 1, 1B and 13 are converted to the corresponding 1-oxides by the above procedure.

The same compound is obtained by reaction of 0.1 mole chloromethyl 6-alpha-chloropenicillanate in 150 ml. isopropanol containing 0.8 ml. of 0.5 M sodium tungstate (Na$_2$WO$_4$) or an equivalent amount of potassium molybdate (K$_2$MoO$_4$) with 0.1 mole of hydrogen peroxide (30%). The peroxide is added slowly to the other reagents at 60° C., after which the mixture is allowed to cool while stirring overnight. The product is isolated as described above.

EXAMPLE 15

Chloromethyl 6-alpha-chloropenicillanate 1,1-Dioxide

To a solution of 2.83 g., 0.01 mole chloromethyl 6-alpha-chloropenicillanate in 50 ml. of chloroform is added 4.32 g. (0.025 mole) m-chloroperbenzoic acid and the mixture is stirred under a nitrogen atmosphere for 36 hours at room temperature. The solvent is evaporated in vacuo, the residue partitioned between ethyl acetate and water at pH 6.0 and sodium bisulfite is added until a test for the presence of peroxides is negative. The pH is adjusted to 8.0, the layers separated and the organic phase is washed with brine, dried (Na$_2$SO$_4$) and evaporated to dryness in vacuo to provide the title compound.

Alternatively, the title compound is obtained by oxidation of the same starting material in methanol or ethanol containing a catalytic amount of sodium tungstate and addition of 2 molar equivalents of hydrogen peroxide at temperatures of from 20° to 60° C.

In like manner the remaining penicillanate esters provided in Example 13 are converted to the corresponding 1,1-dioxides by the above procedures.

Similarly, the remaining chloromethyl-6-substituted (and 6,6-disubstituted) penicillanate 1-oxides provided in Example 14 are converted to 1,1-dioxides by the above procedure employing one half the amount of m-chloroperbenzoic acid, or by employing an equimolar amount of peracetic acid.

EXAMPLE 16

Chloromethyl penicillanate 1,1-Dioxide

A solution of 4.0 g. (12.7 mmole) chloromethyl 6-alpha-chloropenicillanate 1,1-dioxide in 50 ml. tetrahydrofuran is combined with a solution of 1 g. sodium bicarbonate in 50 ml. water and 2.0 g. of a 50% wet palladium-on-carbon catalyst is added. The mixture is agitated under hydrogen at 50 psi (3.52 kg/cm$^2$) for 20 minutes and the product isolated as described in Example 11.

EXAMPLE 17

Chloromethyl penicillanate 1-Oxide

Chloromethyl 6-alpha-chloropenicillanate 1-oxide is subjected to hydrogenolysis employing the procedures of Examples 11A, 11B or 16 to provide the title compound.

Similarly, the remaining chloromethyl 6-halosubstituted or 6,6-dihalo-substituted penicillanate 1-oxides provided in Example 14 provide the title compound by means of the procedures of Examples 10A, 10B, 11A, 11B or 16.

EXAMPLE 18

Chloromethyl penicillanate 1,1-Dioxide

To a solution of 249 mg. (1.0 mmole) chloromethyl penicillanic acid 1-oxide in 50 ml. methylethyl ketone is added 20 ml. water and the mixture adjusted to pH 5 with phosphoric acid. Then 158 mg. (1.0 mmole) potassium permanganate is added and the mixture stirred at 10° C. for 30 minutes and the reaction mixture worked-up as described in Example 2A to provide the title compound.

When the above procedure is repeated, but employing acetone, tetrahydrofuran or ethyl acetate as solvent in place of methylethylketone, or employing temperatures of from −30° C. to 50° C., the title compound is obtained in like manner. Of course, when the reaction is carried out at −30° C. a longer reaction time is required. Conversely, at 50° C. the reaction time is considerably less than 30 minutes.

The title compound is also provided by oxidation of chloromethyl penicillanic acid 1-oxide with an equimolar amount of hydrogen peroxide or peracid by the procedures of Example 14.

EXAMPLE 19

Chloromethyl penicillanic Acid

A mixture of 1.3 g. (3.2 mmole) chloromethyl 6,6-dibromopenicillanate, 25 ml. ethyl acetate, 25 ml. 1 N sodium bicarbonate and 1.3 g. 10% palladium-on-carbon catalyst was hydrogenated with vigorous shaking at 50 psi (3.52 kg/cm$^2$). After 20 minutes the hydrogen uptake was 4 psi (0.28 kg/cm$^2$). The catalyst was removed by filtration through diatomaceous earth, the layers separated and the aqueous phase extracted with 2×25 ml. ethyl acetate. The combined organic layers were dried (Na$_2$SO$_4$) and solvent removed in vacuo to provide 418 mg. yellow oil. The oil was chromatographed on a column of silica gel (5 g.) eluting with ethyl acetate/hexane 1:1 (v/v). The combined product-containing fractions were evaporated in vacuo to afford 174 mg. of the title compound as an oil. Mass spectrum (m/e) 249 (molecular ion).

The products provided in Example 1B are reacted by the above procedure or the procedures of Examples 10A or 10B to provide compounds of the formula below where X is as defined in Example 1B.

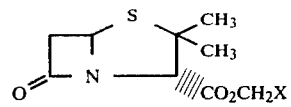

EXAMPLE 20

Chloromethyl penicillanate 1,1-Dioxide

Chloromethyl penicillanic acid is reacted with from 2 to 6 moles of m-chloroperbenzoic acid by the procedure of Example 2 but employing either dichloromethane, chloroform, 1,2-dichloroethane, diethyl ether, tetrahydrofuran, 1,2-dimethoxyethane or ethyl acetate as solvent and reaction temperatures of from −30° to 50° C. to provide the title compound. Similarly, the oxidation is carried out with potassium permanganate or sodium permanganate by the procedure of Example 2A.

Employing the remaining compounds provided in Example 19 as starting material in the above procedures, the following compounds are obtained in like manner.

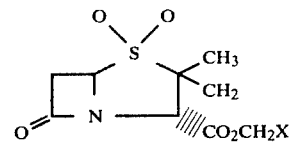

X is as defined in Example 1B.

EXAMPLE 21

Chloromethyl 6-isocyanopenicillanate

6-Isocyanopenicillanic acid is prepared by reacting benzyl 6-formylaminopenicillanate in methylene chloride with phosgene at −40° to −50° C. in the presence of N-methylmorpholine to provide benzyl 6-isocyanopenicillanate and hydrogenolysis over Raney nickel catalyst by procedures described in U.S. Pat. No. 3,996,235.

The 6-isocyanopenicillanic acid is then esterified by the procedure of Example 15 to provide the desired ester.

Alternatively, 6-formylaminopenicillanic acid is esterified by the procedure of Example 15 and the resulting chloromethyl 6-formylaminopenicillanate reacted with phosgene as described above or with an equimolar amount of p-toluenesulfonyl chloride in a solvent amount of pyridine at 0° to 30° C. by the analogous method of Barton et al., J. Chem. Soc. (London) Perkin I, 2657 (1980). In each case the above title compound is obtained.

EXAMPLE 22

6-Isocyanopenicillanic Acid 1,1-Dioxide

6-Isocyanopenicillanic acid is oxidized by the procedure of Example 5 to provide the title compound.

EXAMPLE 23

Chloromethyl 6-isocyanopenicillanate 1,1-Dioxide

A. The title compound is provided by oxidation of chloromethyl 6-isocyanopenicillanate by the methods of Example 2 or Example 2A.

B. Alternatively, the desired product is obtained by esterification of 6-isocyanopenicillanic acid 1,1-dioxide by the method of Example 1 or the method of Example 9.

In like manner the following compounds are prepared by the procedure of Example 1.

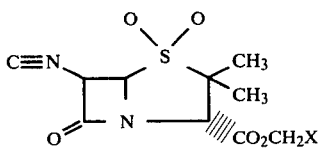

where X is as defined below.

| X | X | X |
| --- | --- | --- |
| Br | n-$C_4H_9SO_2O$ | 3-$ClC_6H_4SO_2O$ |
| I | $(CH_3)_2CH(CH_2)_2SO_2O$ | 2-$BrC_6H_4SO_2O$ |
| $CH_3SO_2O$ | $CH_3(CH_2)_3CH(CH_3)SO_2O$ | 4-$IC_6H_4SO_2O$ |
| $C_2H_5SO_2O$ | 4-$CH_3C_6H_4SO_2O$ | 2-$CH_3OC_6H_4SO_2O$ |

EXAMPLE 24

Chloromethyl 6-Isocyanopenicillanate 1-Oxide

Oxidation of chloromethyl 6-isocyanopenicillanate with one mole of m-chloroperbenzoic acid by the procedure of Example 14 affords the title compound.

EXAMPLE 25

Chloromethyl penicillanate

A solution of 265 mg. (1 mmole) chloromethyl 6-isocyanopenicillanate in dry benzene (15 ml.) is treated with 33 mg. (0.2 mmmole) 2,2'-azobisisobutyronitrile followed by 320 mg. (1.09 mmole) tri-n-butyltin hydride and the mixture heated under a nitrogen atmosphere at reflux for one hour. Removal of solvent under reduced pressure affords the crude title compound which is purified by silica gel chromatography.

EXAMPLE 26

Chloromethyl penicillanate 1-Oxide

Treatment of chloromethyl 6-isocyanopenicillanate 1-oxide by the procedure of Example 25 affords the title compound in like manner.

EXAMPLE 27

Chloromethyl 6-isothiocyanatopenicillanate

A. Chloromethyl 6-benzyloxycarbonylaminopenicillanate

6-Benzyloxycarbonylaminopenicillanic acid is esterified with chloromethyl chlorosulfate by the procedure of Example 13 to provide the desired product.

B. Chloromethyl 6-aminopenicillanate

A solution of chloromethyl 6-benzyloxycarbonylaminopenicillanate (5 g.) in 100 ml. tetrahydrofuran is hydrogenated over 10% Pd/C (1 g.) at 3-4 atmospheres pressure until hydrogen uptake ceases. The catalyst is removed by filtration, the filtrate extracted with 1 N hydrogen chloride, the aqueous layer adjusted to pH 9 with sodium carbonate and extracted with ethyl ether. The ether extract is dried ($MgSO_4$) and evaporated to dryness to provide the desired amino ester which is used in the next step.

C. A solution of 4.0 g. (15 mmole) chloromethyl 6-aminopenicillanate in 75 ml. methylene chloride is added slowly at 0° to 5° C. to a mixture of 2.30 g. (20 mmole) thiophosgene, 25 ml. methylene chloride, 2.0 g. (20 mmole) calcium carbonate and 25 ml. water. When the addition is complete, the resulting mixture is stirred at 0°-5° C. for one hour, overnight at 20° C., and finally at 35° C. for one hour. The reaction mixture is filtered, the organic layer separated and washed with dilute hydrochloric acid, water and dried ($MgSO_4$). The solvent is evaporated in vacuo to provide the desired product.

EXAMPLE 28

A. A solution of 0.43 g. (2.04 mmole) dicyclohexylcarbodiimide and 1 ml. carbon disulfide in 50 ml. dry tetrahydrofuran is cooled to −10° C. and a solution of 432 mg. (2.0 mmole) 6-aminopenicillanic acid in dry tetrahydrofuran is added. The resulting mixture is warmed slowly to room temperature, filtered and the solvent evaporated to provide 6-isothiocyanatopenicillanic acid.

Use of 6-aminopenicillanic acid 1-alpha-oxide, the corresponding 1-beta-oxide or 6-aminopenicillanic acid 1,1-dioxide in place of 6-aminopenicillanic acid in the above procedure provides, respectively, 6-isothiocyanatopenicillanic acid 1-alpha-oxide, 6-isothiocyanatopenicillanic acid 1-beta-oxide and 6-isothiocyanatopenicillanic acid 1,1-dioxide.

B. Esterification of the 6-isothiocyanatopenicillanic acid and the above oxides by the procedure of Example 1, 1B or 13 affords the following compounds

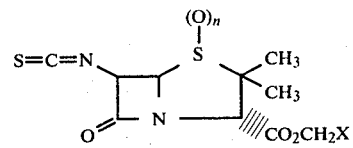

where n is zero, 1 or 2 and X is as defined in Examples 1, 1B, and 13.

EXAMPLE 29

Chloromethyl 6-Isothiocyanatopenicillanate 1,1-Dioxide

A. 6-Benzyloxycarbonylaminopenicillanic acid 1,1-dioxide

To a stirred solution of 63.5 g. benzyloxycarbonylaminopenicillanic acid (63.5 g.) and potassium bicarbonate (18.1 g.) in water (1125 ml.) is slowly added at 0° C. a solution of 38 g. potassium permanganate in 915 ml. water. The mixture is maintained at pH 6.5 by addition of dilute sulfuric acid while stirring. When oxidation is complete, the mixture is filtered, the filtrate extracted with ethyl ether. The aqueous phase is filtered, 600 ml. ethyl acetate added and acidified (pH 2.5) with stirring. The organic layer is separated, the aqueous layer extracted with 2×300 ml. ethyl acetate and the combined organic phase dried ($Na_2SO_4$). The solvent is evaporated in vacuo and the residue crystallized from ethyl acetate-petroleum ether to afford the purified product, M.P. 153°–154° C.

B. The 6-benzyloxycarbonylaminopenicillanic acid 1,1-dioxide obtained above is converted to the corresponding chloromethyl ester by the procedure of Example 27, part A. The amino protecting group is removed by hydrogenolysis by the procedure of Example 27, part B to provide chloromethyl 6-aminopenicillanate 1,1-dioxide. The latter compound is then treated with thiophosgene by the method of Example 27, part C to provide chloromethyl 6-isothiocyanatopenicillanate 1,1-dioxide.

EXAMPLE 30

Chloromethyl penicillanate 1,1-Dioxide

To a solution of 27.3 g. (0.10 mole) chloromethyl 6-isocyanopenicillanate 1,1-dioxide in 750 ml. benzene is added 100 mg. azobisisobutyronitrile and 31.9 g. (0.11 mole) tri-n-butyltin hydride. The solution is heated under nitrogen to reflux and held at this temperature for 25 minutes. The solvent is evaporated in vacuo and the residue purified by silica gel chromatography to provide the desired product.

When an equimolar amount of chloromethyl 6-isothiocyanatopenicillanate 1,1-dioxide is used in place of the 6-isocyano compound employed above, and twice the above amount of tri-n-butyltin hydride, chloromethylpenicillanate 1,1-dioxide is obtained in like manner.

Similarly, the compounds provided in Example 23 yield compounds of the formula below wherein X is as defined in Example 23.

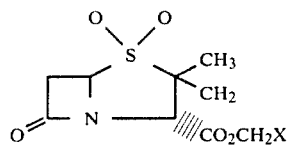

EXAMPLE 31

Chloromethyl penicillanate and the remaining halomethyl and sulfonyloxymethyl esters provided in Examples 19 and 25 are oxidized by the procedures of Examples 2 or 2A to provide compounds of the formula

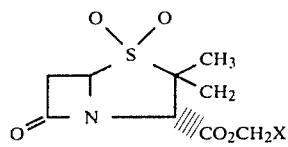

EXAMPLE 32

Oxidation of chloromethyl penicillanate 1-oxide by the procedure of Example 14 affords chloromethyl penicillanate 1,1-dioxide.

EXAMPLE 33

Chloromethyl 6-chloro-6-phenylselenylpenicillanate

A. Chloromethyl 6-phenylacetamidopenicillanate

Phenylacetamido penicillanic acid is esterified by the procedure of Example 13 to provide the desired chloromethyl ester.

B. Chloromethyl 6-N-nitrosophenylacetamidopenicillanate

To a mixture of 25.7 g. (0.067 mole) chloromethyl 6-phenylacetamidopenicillanate, 66 g. (0.8 mole) sodium acetate and 350 ml. methylene chloride is added a solution of 10 g. (0.11 mole) dinitrogen tetraoxide in 125 ml. methylene chloride. After stirring at −5° C. for 45 minutes, another 10 g. portion of dinitrogen tetraoxide in 125 ml. solvent is added and stirring continued for 45 minutes. The mixture is slowly poured into a solution of 60 g. sodium bicarbonate in 500 ml. water, with stirring over 30 minutes. The organic layer is separated, washed with aqueous sodium bicarbonate, water, dried ($MgSO_4$) and the solvent evaporated to half volume. The solution is used in the next step.

C. Chloromethyl 6-diazopenicillanate

The solution from part B is refluxed for four hours, allowed to cool, washed with aqueous sodium bicarbonate, water, dried ($MgSO_4$) and the solvent evaporated in vacuo to afford the crude diazo compound which is used in the next step without purification.

D. To a solution of 2.8 g. (0.01 mole) chloromethyl 6-diazopenicillanate in 100 ml. methylene chloride and maintained under a nitrogen atmosphere is slowly added a solution of 1.92 g. (0.01 mole) phenylselenyl chloride in 50 ml. methylene chloride. Evolution of nitrogen and simultaneous decolorization of the phenylselenyl chloride takes place. The mixture is stirred at room temperature for 15–20 minutes after the addition is complete, the solvent is removed in vacuo and the residue purified by column chromatography on silica gel.

EXAMPLE 34

The procedures of Example 33 are repeated except as follows:

1. The esterification step in part A is carried out by the procedure of Example 1 employing chloroiodomethane or one of the remaining dihalomethanes, di(alkylsulfonyloxy)methanes or di(arylsulfonyloxy)methanes described in Example 1.

2. In the procedure of part D, an equimolar amount of reagent of formula $R^2C_6H_4SeCl$ or corresponding arylselenyl bromide is employed in place of phenylselenyl chloride. The arylselenyl halides are prepared by halogenolysis of the corresponding diselenide with chlorine, bromine, thionyl chloride or sulfuryl chloride, or treatment of the appropriate selenenic with hydrobromic acid by methods reviewed in "Comprehensive Organic Chemistry", Barton and Ollis, Editors, Pergamon Press, New York, 1979, Vol. 3, p. 509.

In each case the products obtained are of the formula

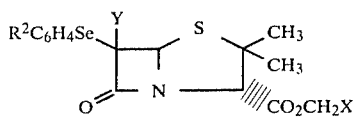

where Y, $R^2$ and X are defined below.

| Y | $R^2$ | X |
|---|---|---|
| Br | H | Cl |
| Cl | 4-Cl | $CH_3SO_2O$ |

-continued

| Y | R² | X |
|---|---|---|
| Br | 3-Br | Br |
| Br | 4-I | I |
| Cl | 4-NO₂ | i-C₄H₉SO₂O |
| Cl | 4-CH₃ | n-C₆H₁₃SO₂O |
| Cl | 2-C₂H₅ | 4-ClC₆H₄SO₂O |
| Cl | 3-i-C₃H₇ | 2-BrC₆H₄SO₂O |
| Cl | 2-CH₃O | 4-IC₆H₄SO₂O |
| Cl | 4-n-C₃H₇O | 3-NO₂C₆H₄SO₂O |
| Cl | 4-C₂H₅O | 4-CH₃C₆H₄SO₂O |
| Br | 2-C₂H₅O | 3-(CH₃)₂CHC₆H₄SO₂O |
| Br | 2-CH₃ | 4-CH₃OC₆H₄SO₂O |
| Cl | H | 3-C₂H₅OC₆H₄SO₂O |
| Cl | H | 4-n-C₃H₇OC₆H₄SO₂O |

EXAMPLE 35

Chloromethyl 6-chloro-6-phenylselenylpenicillanate 1,1-Dioxide

To an ice cold solution of 741 mg. (3 mmole) chloromethyl 6-aminopenicillanate 1,1-dioxide in 75 ml. methylene chloride is added in succession, 75 ml. ice water, 232.5 mg. (3.37 mmole) sodium nitrite and 3 ml. 1 N perchloric acid. The resulting mixture is stirred at 0° C. for two hours, the organic layer is separated, washed with cold brine, dried and concentrated to about 25 ml. To this solution of chloromethyl 6-diazopenicillanate 1,1-dioxide is slowly added a solution of 576 mg. (3 mmole) phenylselenyl chloride in 25 ml. methylene chloride. When gas evolution is complete the mixture is stirred at room temperature for one hour. Evaporation of solvent provides the crude product which is purified by chromatography on silica gel.

Use of chloromethyl 6-aminopenicillanate 1-oxide in place of the above 1,1-dioxide as starting material in the above procedure affords chloromethyl 6-chloro-6-phenylselenylpenicillanate 1-oxide.

Similarly, sulfones of the formula below, and the corresponding sulfoxides are obtained from the appropriate starting materials in each case by the above procedure.

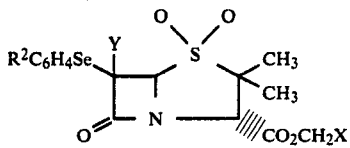

where Y, R² and X are as defined in Example 34.

EXAMPLE 36

Chloromethyl penicillanate 1,1-Dioxide

To a solution of 1.0 g. (2.1 mmole) chloromethyl 6-chloro-6-phenylselenylpenicillanate 1,1-dioxide in 25 ml. toluene is added 75 mg. azobisisobutyronitrile and 1.75 g. (5 mmole) triphenyltin hydride. The mixture is heated under nitrogen at 100° C. for two hours. The toluene evaporated in vacuo and the residue chromatographed on silica gel to provide the desired product.

Use of an equivalent amount of either tri-n-butyltin hydride or other trialkyltin hydride, triaryltin hydride or dialkyltin dihydride employed in Example 10 affords similar results.

When the above procedure is carried out with the above tin hydrides in benzene, chlorobenzene, ethyl ether, tetrahydrofuran or dioxane as solvent and employing the above starting penicillanate ester or one of the compounds provided in Example 35, at temperatures of from room temperature up to the boiling point of the solvent, the following compounds are obtained where X is as defined in Example 35.

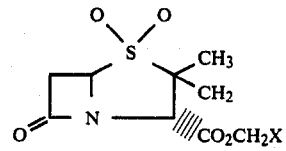

EXAMPLE 37

When the procedures of Example 36 are carried out, but employing one of the products of Examples 33, 34 or a corresponding sulfoxide as starting material in place of chloromethyl 6-chloro-6-phenylselenylpenicillanate 1,1-dioxide, and the resulting penicillanate ester or penicillanate-1-oxide ester is oxidized by the method of Example 2, 5 or 18, the following sulfones are similarly obtained.

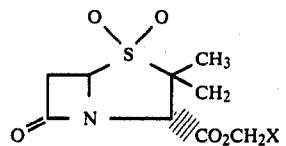

where X is as defined for the starting 6-halo-6-arylselenylpenicillanate.

EXAMPLE 38

6'-(2-Benzyloxycarbonylamino-2-phenylacetamido)-penicillanoyloxymethyl Penicillanate 1,1-Dioxide To a stirred solution of 1.9 g. of potassium 6-(2-benzyloxycarbonylamino-2-phenylacetamido)penicillanate in 30 ml. of dimethyl sulfoxide was added 930 mg. of chloromethyl penicillanate 1,1-dioxide followed by a few milligrams of sodium iodide. Stirring was continued at ambient temperature overnight, and then the reaction mixture was poured into 60 ml. of water. The pH was raised to 8.5 and the product was extracted into ethyl acetate. The extracts were washed with water and with saturated sodium chloride solution, and then they were dried (Na₂SO₄). Evaporation of the ethyl acetate in vacuo gave 800 mg. of crude product.

The crude product was purified by chromatography on silica gel, using 1:1 ethyl acetate-hexane as eluant, to give 440 mg. of the title compound (18% yield). The NMR spectrum of the product (CDCl₃) showed absorptions at 7.4 (m, 10H), 7.1 (d, 1H, J=8 Hz), 6.2 (d, 1H, J=8 Hz), 5.9 (s, 2H), 5.7–5.2 (m, 3H), 5.1 (s, 2H), 4.6 (t, 1H), 4.4 (s, 2H), 3.4 (d, 2H) and 1.7–1.2 (m, 12H) ppm.

EXAMPLE 39

6'-(2-Amino-2-phenylacetamido)penicillanoyloxymethyl Penicillanate 1,1-Dioxide

To a solution of 1.6 g. of 6'-(2-benzyloxycarbonylamino-2-phenylacetamido)penicilanoyloxymethyl penicillanate 1,1-dioxide in 100 ml. of tetrahydrofuran and 80 ml. of water was added 0.12 ml. of glacial acetic acid followed by 1.6 g. of 10% palladium-on-carbon. The mixture was shaken under an atmosphere of hydrogen at a pressure of ca. 50 psig (3.2 kg./cm.²) for 1.5 hours. At this point the catalyst was removed by filtration and 1.6 g. of fresh catalyst was added. The mixture was shaken under hydrogen at ca. 50 psig for a further 1 hour. The catalyst was removed by filtration and the bulk of the tetrahydrofuran was removed by evaporation in vacuo. The pH of the residual aqueous phase was lowered to 2.0 using 6 N hydrochloric acid and the acidified solution was extracted with ethyl acetate. The extracts were dried ($Na_2SO_4$) and evaporated in vacuo to give 500 mg. of impure starting material. The pH of the above acidified solution was raised to 8.5 and then it was further extracted with ethyl acetate. The latter extracts were combined, dried ($Na_2SO_4$) and evaporated in vacuo. The residue was dissolved in 3 ml. of ethyl acetate, and the resulting solution was added dropwise to 40 ml. of hexane. The solid which precipitated was recovered by filtration to give 500 mg. of crude product.

The crude product was purified by chromatography on silica gel, using ethyl acetate as eluant, to give a 40% yield of the title compound. The IR spectrum (KBr disc) showed an absorption at 1802 cm$^{-1}$. The NMR spectrum (CDCl$_3$) showed absorptions at 8.1 (d, 1H, J=6 Hz), 7.4 (s, 4H), 5.9 (q, 2H), 5.7–5.5 (m, 2H), 4.75–4.6 (m, 2H), 4.55 (s, 1H), 4.45 (s, 1H), 3.55 (d, 2H), 1.6 (d, 6H) and 1.5 (d, 6H) ppm.

We claim:

1. A compound of the formula

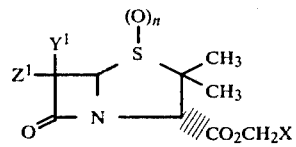

wherein X is Cl, Br, I or $OSO_2R^1$ where $R^1$ is alkyl having from one to six carbon atoms or $C_6H_4R^2$ where $R^2$ is H, Cl, Br, I, $NO_2$ or alkyl or alkoxy having from one to three carbon atoms; n is zero, 1 or 2; $Y^1$ is H and $Z^1$ is C≡N— or SCN—, or $Y^1$ is $SeC_6H_4R^2$ and $Z^1$ is Cl or Br, $R^2$ is H, Cl, Br, I, $NO_2$ or alkyl or alkoxy having from one to three carbon atoms.

2. A compound according to claim 1 wherein n is zero, $Y^1$ is H and $Z^1$ is C≡N— or SCN—.

3. A compound according to claim 2 wherein X is Cl or $OSO_2R^1$ where $R^1$ is $CH_3$ or 4-tolyl.

4. A compound according to claim 1 wherein n is 2, $Y^1$ is H and $Z^1$ is C≡N— or SCN—.

5. A compound according to claim 4 wherein X is Cl, $OSO_2CH_3$ or 4-tolyl-$SO_2O$.

6. A compound according to claim 1 wherein $Y^1$ is $SeC_6H_5$ and $Z^1$ is Cl.

7. A compound according to claim 6 wherein X is Cl, $OSO_2CH_3$ or 4-tolyl-$SO_2O$.

8. A compound according to claim 7 wherein X is Cl.

* * * * *